United States Patent

Moriya

[11] Patent Number: 5,892,241
[45] Date of Patent: Apr. 6, 1999

[54] APPARATUS AND METHOD FOR THE INSPECTION OF SCATTERED RESIST

[75] Inventor: Kazuo Moriya, Atago, Japan

[73] Assignee: Mitsui Mining & Smelting Co., Ltd., Tokyo, Japan

[21] Appl. No.: 899,119

[22] Filed: Jul. 23, 1997

[30] Foreign Application Priority Data

Aug. 1, 1996 [JP] Japan ................................. 8-218125

[51] Int. Cl.$^6$ .................................................. G01N 21/86
[52] U.S. Cl. .................................. 250/559.4; 250/559.41; 250/559.45; 250/226; 356/237.4
[58] Field of Search ........................... 250/559.4, 559.41, 250/559.45, 559.44, 559.46, 226; 356/237.3, 237.4, 237.5

[56] References Cited

U.S. PATENT DOCUMENTS 5,032,735  7/1991  Kobayashi et al. ................ 250/559.34

*Primary Examiner*—Que T. Le
*Attorney, Agent, or Firm*—Kubovcik & Kubovcik

[57] ABSTRACT

A resist scattered on and attached to unwanted portions is stably detected. A target inspection region including the unwanted portions to which the scattered resist should not be attached is illuminated with white light to obtain a color image, and a region having the same hue and chroma as a resist is detected. The target inspection region may be illuminated with light containing a first wavelength light exhibiting high reflectance for the unwanted portions and high absorbance for the resist and a second wavelength light exhibiting high reflectance for the unwanted portions and high transmittance for the resist to detect a color image obtained with the second wavelength light from the images of the target inspection region which are obtained by illumination with the illumination light. The resist attached to the unwanted portions may be detected on the basis of the contrast of the image obtained upon illumination with only the first wavelength light. The image of a resist-attached portion is extracted as a portion having lightness not more than a predetermined value from the images of the target inspection region which are obtained by illumination with the first wavelength light, and there is extracted the image of the scattered resist attached to the unwanted portions which are common to both the image of the unwanted portions having no scattered resist thereon, said image being obtained upon illumination of the target inspection region with the second wavelength light, and the image of the resist-attached portions.

16 Claims, 4 Drawing Sheets

APPARATUS AND METHOD FOR THE INSPECTION OF SCATTERED RESIST

BACKGROUND OF THE INVENTION

1. Field of the Invention

The present invention relates to an apparatus and method for detecting a resist scattered on and attached to unwanted portions of a TAB tape (tape automated bonding) or circuit board.

2. Description of the Prior Art

A resist material is generally printed to form an insulating or protective film on a TAB tape or circuit board. This printing is performed by silk printing or the like.

In printing a resist material by silk printing or the like, the resist material may scatter on and attach to unwanted portions. The resist so scattered and attached will cause unsatisfactory turning on electricity in an electronic circuit. Even if the amount of resist scattered on and attached to the unwanted portions is small, it is necessary to detect such resist in order to prevent such a fault.

SUMMARY OF THE INVENTION

It is an object of the present invention to provide an inspection apparatus and method capable of easily detecting a resist scattered on and attached to such unwanted portions.

In order to achieve the above object, there is provided a resist scattering inspection apparatus comprising illumination means for illuminating, with white light, a target inspection region including unwanted portions to which no scattered resist must be attached, and resist detection means for picking up a color image of the target inspection region to obtain image data, and detecting a region having the same hue and chroma or saturation as those of the resist on said image on the basis of the image data.

According to the present invention, there is also provided a resist scattering inspection method comprising the steps of illuminating, with white light, a target inspection region including unwanted portions to which no scattered resist must be attached, and picking up a color image of the target inspection region to obtain image data and detecting a region having the same hue and chroma as those of the resist on said image on the basis of the image data.

According to the present invention, there is provided another resist scattering inspection apparatus comprising illumination means for illuminating a target inspection region including unwanted portions to which no scattered resist must be attached, with illumination light containing a first wavelength light exhibiting high reflectance for the unwanted portions and high absorbance for the resist and a second wavelength light exhibiting high reflectance for the unwanted portions and high transmittance for the resist, and detection means for detecting a color image of the second wavelength light from an image illuminated with the illumination light in the target inspection region.

According to the present invention, there is provided another resist scattering inspection method comprising the steps of illuminating a target inspection region including unwanted portions to which no scattered resist must be attached, with illumination light containing a first wavelength light exhibiting high reflectance for the unwanted portions and high absorbance for the resist and a second wavelength light exhibiting high reflectance for the unwanted portions and high transmittance for the resist, and detecting a color image of the second wavelength light from an image illuminated with the illumination light in the target inspection region.

According to the present invention, there is provided still another resist scattering inspection apparatus comprising illumination means for illuminating a target inspection region including unwanted portions to which no scattered resist must be attached, with illumination light exhibiting high reflectance for the unwanted portions and high absorbance for the resist, and detection means for detecting the resist attached to the unwanted portions in accordance with the contrast of an image obtained by the illumination light in the target inspection region.

According to the present invention, there is provided still another resist scattering inspection method comprising the steps of illuminating a target inspection region including unwanted portions to which no scattered resist must be attached, with illumination light exhibiting high reflectance for the unwanted portions and high absorbance for the resist, and detecting the resist attached to the unwanted portions on the basis of the contrast of an image obtained by the illumination light in the target inspection region.

According to the present invention, there is provided still another resist scattering inspection apparatus which comprises (I) illumination means for illuminating a target inspection region including unwanted portions to which no scattered resist must be attached, respectively with a first wavelength light exhibiting high reflectance for the unwanted portions and high absorbance for the resist and a second wavelength light exhibiting high reflectance for the unwanted portions and high transmittance for the resist, and (II) scattered resist detection means comprising (1) extracting an image of said unwanted portions having no scattered resist by illuminating said target inspection region with said second wavelength light, (2) extracting an image of resist-attached portions as portions having lightness not more than a predetermined value from an image of said target inspection region obtained by illuminating said target inspection region with said first wavelength light, and then (3) extracting an image of said scattered resist portions attached to said unwanted portions as portions which are common to the image of said unwanted portions and the image of the resist-attached portions.

According to the present invention, there is provided still another resist scattering inspection method comprising the steps of (I) extracting an image of resist-attached portions as portions having lightness not more than a predetermined value from an image of a target inspection region including unwanted portions obtained by illumination with a first wavelength light, the unwanted portions being those to which no scattered resist must be attached, and the first wavelength light exhibiting high reflectance for the unwanted portions and high absorbance for the resist, (II) obtaining an image of said unwanted portions having no scattered resist thereon by illuminating said target inspection region with a second wavelength light having high reflectance for said unwanted region and high transmittance for the resist, and then (III) extracting an image of scattered resist attached to the unwanted portions as portions which are common to the image of said resist-attached portions and the image of the unwanted portions.

DESCRIPTION OF THE PREFERRED EMBODIMENT

Figure 1:
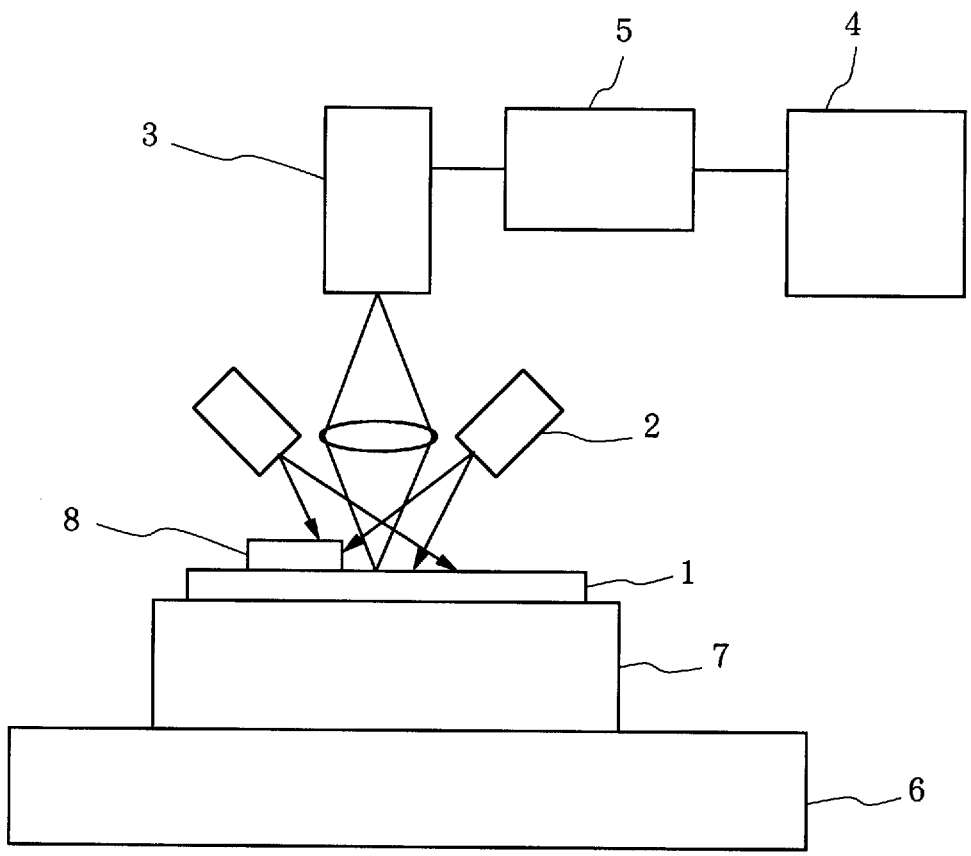
FIG. 1 is a diagram illustrating a resist scattering inspection apparatus according to an embodiment of the present invention.

FIG. 1 is a diagram showing an embodiment of a resist scattering inspection apparatus of the present invention. Referring to FIG. 1, this resist scattering inspection apparatus comprises an illumination means 2, an image pickup means or image sensor means 3, and a resist detection means 5. The illumination means 2 illuminates, with white light, a target inspection region including an electrode 1 and unwanted portions to which no scattered resist must be attached. The image pickup means 3 picks up a color image of the target inspection region. The resist detection means 5 detects a region having a hue and chroma (or saturation) which are equal to those of a resist on an image obtained from the image pickup means 3, on the basis of the image data obtained from the means 3 and displays this detected region on a monitor 4. The image pickup means comprises an RGB (red, green, blue) three-chip CCD camera preferably free from pixel shifts.

The resist detection means 5 may comprise a color extraction apparatus PICOLOR (tradename) available from K.K. ADS. This color extraction apparatus converts a video signal RGB from the image pickup means into a luminance signal Y and two color difference signals R-Y and B-Y. The color extraction apparatus uses the color difference signals R-Y and B-Y to express the color components in accordance with the hue and saturation which are independent of the lightness, thereby extracting a color. According to this apparatus, even if the lightness component changes due to the illuminance of the illumination light, the hue and saturation (or chroma) do not change. For this reason, a region having the same hue and saturation as those of the resist can be stably detected.

In inspection, teaching of the hue and saturation of a resist for which color extraction is to be done is preliminarily performed for the resist detection means 5. More specifically, the target inspection region on a substrate 7 serving as a sample is positioned within the visual field of the image pickup means 3 by an X-Y stage 6 and illuminated with the illumination means 2, thereby to display an image represented by the hue and saturation of the target inspection region on the monitor 4 through the image pickup means 3 and the resist detection means 5. An arbitrary region within the resist region in the image is designated with a mouse or the like to store the same hue and saturation as those of a resist 8 in the resist detection means 5. At this time, the color difference colorimetric chart and the positionings of the hue and saturation of the designated arbitrary region in this chart are displayed on the monitor 4 and, by reference to these data displayed, the hue and saturation to be detected can be set with an arbitrary width. The color difference colorimetric chart displayed on the monitor 4 is exemplarily displayed by continuously changing the hue and saturation using them as parameters. Arbitrary positions on the chart are designated with a mouse (pointer) or the like to easily specify a range of detection of the hue and saturation.

After such teaching as above, an actual target inspection region is positioned within the visual field of the image pickup means 3 by the X-Y stage 6 and, at this point, the target inspection region is displayed on the monitor 4 in the same manner as described above. At this time, a portions corresponding to the hue and saturation within the above detection range, i.e., the resist portions is displayed in a binary image using a specific color, e.g., white. Therefore, the resist scattered on the unwanted portions of the electrode 1 can be easily recognized.

Note that the resist detection means 5 may comprise a color image extraction apparatus KA-100 (tradename) available from KURABO INDUSTRIES LTD., Japan in addition to the above example A colored resist can be inspected as described above. A resist such as a polyimide resin resist, however, may be transparent or light in color, and in this case it will be difficult to recognize such a resist as a color difference in a case where the resist does not contain any pigment. In this case, as illumination means 2 there may be used means for illuminating a target inspection region including unwanted portions with light containing a first wavelength light exhibiting high reflectance for the electrode 1 and high absorbance for the resist and a second wavelength light exhibiting high reflectance for the unwanted portions and high transmittance for the resist, thereby to detect an image having the color of the second wavelength light by the resist detection means 5 from the image of the target inspection region which are obtained by illumination with the illumination light.

Figure 2:
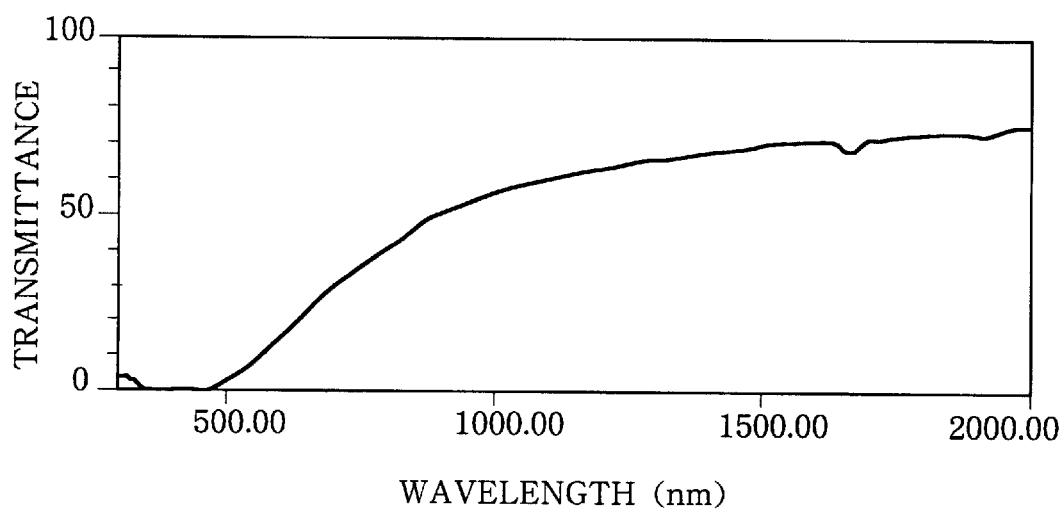
FIG. 2 is a graph illustrating variation of transmittance of a resist with every change of wavelength.
Figure 3:
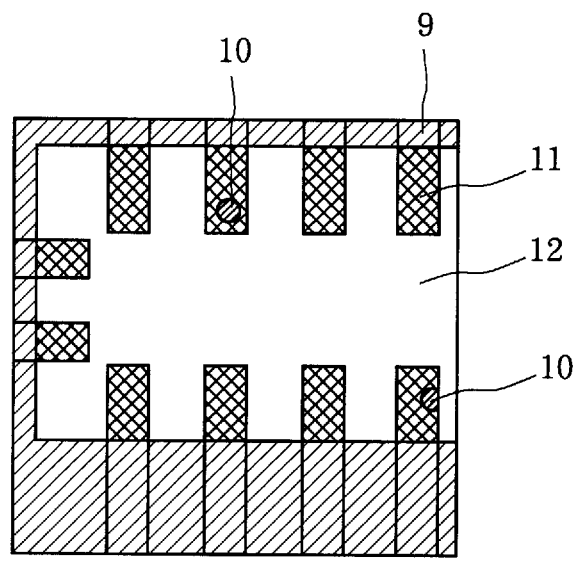
FIG. 3 is a view showing the image of a target inspection region when the region is illuminated with illumination light containing red light and blue light.
Figure 4:
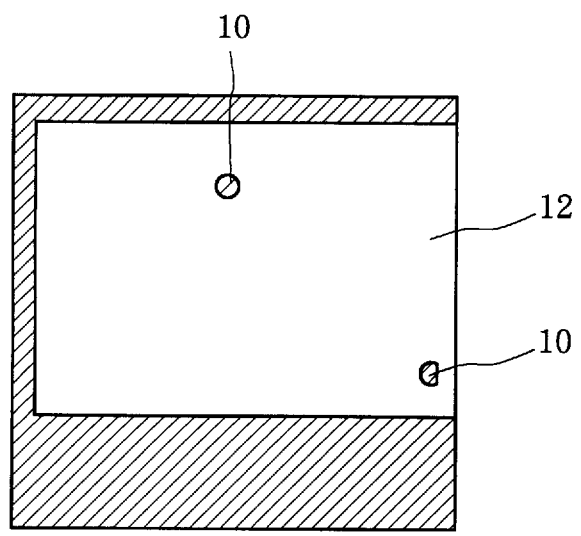
FIG. 4 is a view showing an image obtained by color-extracting the image in FIG. 3.

For a transparent or light-color resist, the transmittance of light for the resist will change with respect to the wavelength of the light used, e.g., as shown in FIG. 2. That is, the transmittance decreases on the shorter-wavelength side. Blue light and red light can be used as the first wavelength light and the second wavelength light, respectively. In this case, the blue light is absorbed by the resist 8, while the red light passes through the resist 8 and is reflected by the electrode 1. In an image displayed on the monitor 4 without performing color extraction through the image pickup means 3 and the resist detection means 5, electrode portions 9 covered with the resist and electrode portions 10 to each of which scattered resist is attached are displayed in red, while electrode portions 11 to any of which no resist is attached are displayed in purple as a mixture of red and blue, as shown in FIG. 3. The hue and saturation of the electrode portions 9 displayed in red are subjected to above-described teaching thereby to obtain an image from which the color is extracted, with the result that the image so obtained clearly indicates the scattered resist-attached portions 10 as shown in FIG. 4. FIGS. 3 and 4 are those in which TAB tapes are used as examples. Reference numeral 12 in FIGS. 3 and 4 denotes a device hole. In this case, unwanted portions to which no scattered resist must be attached are inner lead (electrode) portions extending into the device hole 12.

The illumination means 2 may perform illumination with wavelength light, e.g., blue light, exhibiting high reflectance for the unwanted portions and high absorbance for the resist to obtain an image, and the resist attached to the unwanted portions may be detected in accordance with the contrast of the image. In this case, in an image simply displayed upon picking up the image of the target inspection region, a part of the unwanted portions to which the resist is attached looks darker than a part of the unwanted portions to which no resist is attached, whereupon a predetermined brightness difference, i.e., contrast is present between these parts. For example, among the inner lead (electrode) portions extending into the device hole 12 in FIG. 3, the electrode portions 10 to which scattered resist is attached look dark because the illumination light is absorbed by the resist. Only the portions 11 to which no scattered resist is attached are displayed in blue. The image pickup means 3 may use a monochrome camera. In this case, the portions 10 to which scattered resist is attached look darker than the electrode portions 11 to which no scattered resist is attached. For this reason, the resist detection means 5 may simply display an image picked up by the image pickup means 3 on the monitor 4. Alternatively, the lightness of the image is binarized with a predetermined threshold value to extract only the resist-attached portions, and then the image so treated may be displayed as shown in FIG. 4. In this case, no color extraction apparatus is used, and inspection can be performed with an inexpensive arrangement.

The illumination means 2 may be one for illuminating a target inspection region respectively with said first wavelength light and said second wavelength light. At the same time, the resist detection means 5 may be one for obtaining an image of the unwanted portions of the inspection region to which no scattered resist is attached upon illumination of the target inspection region with said second wavelength light, extracting an image of resist-attached portions as portions having lightness equal to or less than a predetermined value from images of the target inspection region which are obtained by illumination with the first wavelength light, and then extracting an image of scattered resist portion attached to the unwanted portions which are common to the image of the unwanted portions and the image of the resist-attached portions. In this case, blue light and red light can be used as the first wavelength light and the second wavelength light, respectively, as described above.

Figure 5:
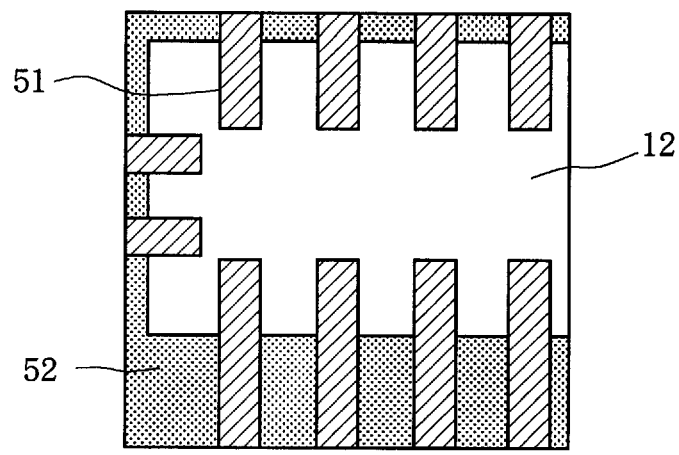
FIG. 5 is a view showing the image of the target inspection region when the region is illuminated with red light.
Figure 6:
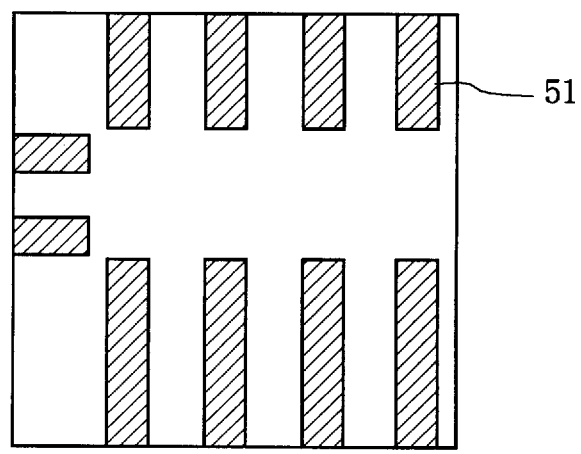
FIG. 6 is an image obtained by binarizing the image in FIG. 5.
Figure 7:
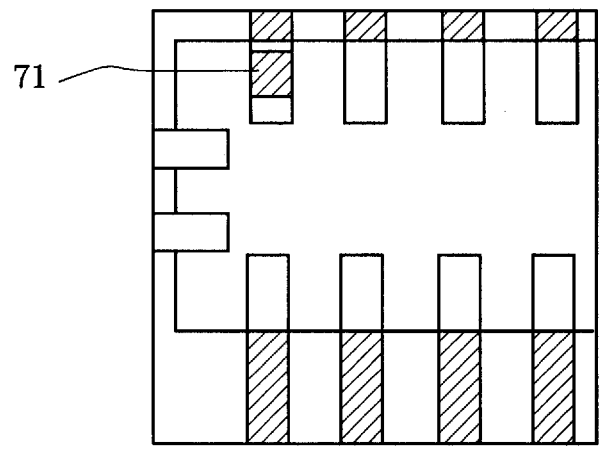
FIG. 7 is a view showing an image obtained by extracting portions which are common to the image in FIG. 6 and a resist portion image obtained by binarizing an image of the target inspection region obtained by illumination of the region with blue light.
Figure 8:
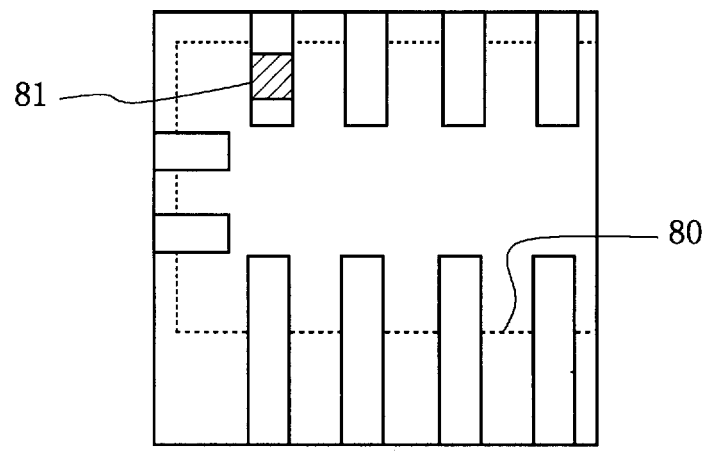
FIG. 8 is a view showing an image obtained by extracting resist portions present only in the unwanted portions on the image in FIG. 7.

In this case, as shown in FIG. 5, the image obtained with the red illumination light is bright at electrode portions 51 and dark at remaining portions 52. For this reason, this image data is binarized with a predetermined threshold value with respect to the lightness to obtain an image consisting of only the electrode portions 51, i.e., the image of portions to which no scattered resist is attached, as shown in FIG. 6. The image obtained with the blue illumination light is dark at portions where the resist is present, and portions except the scattered resist-attached portions of the inner lead portions extending into the device hole 12 are displayed in blue and, thus, the image is binarized with a predetermined threshold value with respect to the lightness to obtain an image of only resist-attached portions. Accordingly, this image data is logically ANDed with the image data shown in FIG. 6 to obtain an image having a hatched portion 71 shown in FIG. 7, i.e., an image of a part of the unwanted portions which has the resist attached thereto. A scattered resist-attached portion in a region 80 in FIG. 8, i.e., in the unwanted portions is extracted from the image in FIG. 8 to obtain an image representing only the scattered resist 81. Note that the region 80 coincides with the device hole 12 portion in this case.

As has been described above, according to the present invention, a region having a hue and saturation equal to those of a resist is detected by a color extraction apparatus and displayed. Therefore, the scattered resist can be stably detected.

A target inspection region including unwanted portions to which no scattered resist must be attached is illuminated with illumination light containing a first wavelength light exhibiting high reflectance for the unwanted portions and high absorbance for the resist and a second wavelength light exhibiting high reflectance for the unwanted portions and high transmittance for the resist to detect an image having the same color as the second wavelength light from images of the target inspection region which are obtained by illumination with the illumination light. Even if the resist is transparent, the scattered resist attached to the unwanted portions can be detected.

A target inspection region including unwanted portions to which no scattered resist must be attached is illuminated with illumination light exhibiting high reflectance for the unwanted portions and high absorbance for the resist to detect the resist attached to the unwanted portions in accordance with the contrast of a target inspection region image obtained by the illumination light. Any scattered resist can be detected with a simple arrangement.

There is extracted an image of resist-attached portions as those having lightness not more than a predetermined value from images of the target inspection region which are obtained by illumination with the first wavelength light, and there is extracted an image of the scattered resist attached to the unwanted portions which are common as a base to an image of scattered resist-free unwanted portions which is obtained by illuminating the target inspection region with the second wavelength light and the image of the resist-attached portions. Therefore, even if the resist is transparent, the scattered resist can be surely detected.

What is claimed is:

1. A resist scattering inspection apparatus comprising illumination means for illuminating, with white light, a target inspection region including unwanted portions to which no scattered resist must be attached, and resist detection means for picking up a color image of the target inspection region to obtain image data, and detecting a region having the same hue and chroma as those of the resist on said image on the basis of the image data.

2. An apparatus according to claim 1, further comprising display means for displaying an image of a detection result obtained by said resist detection means.

3. An apparatus according to claim 1, wherein the unwanted portions are inner lead portions extending into a device hole in tape automated bonding.

4. A resist scattering inspection method comprising the steps of illuminating, with illumination light, a target inspection region including unwanted portions to which no scattered resist must be attached, the illumination light containing a first wavelength light exhibiting high reflectance for the unwanted portions and high absorbance for the resist and a second wavelength light exhibiting high reflectance for the unwanted portions and high transmittance for the resist, and detecting an image having the color of the second wavelength light from images of the target inspection region which are obtained by illuminating the region with the illumination light.

5. A resist scattering inspection apparatus comprising illumination means for illuminating, with illumination light, a target inspection region including unwanted portions to which no scattered resist must be attached, the illumination light exhibiting high reflectance for the unwanted portions and high absorbance for the resist, and detection means for detecting a resist attached to the unwanted portions in accordance with contrast of a target inspection region image obtained by illuminating the region with the illumination light.

6. An apparatus according to claim 5, further comprising display means for displaying an image of a detection result obtained by said detection means.

7. An apparatus according to claim 5, wherein the unwanted portions are inner lead portions extending into a device hole in tape automated bonding.

8. A resist scattering inspection method comprising the steps of extracting an image of resist-attached portions as those having lightness not more than a predetermined value from images of the an unwanted portions-including target inspection region which are obtained by illuminating said region with a first wavelength light, the unwanted portions being those to which no scattered resist must be attached, and the first wavelength light exhibiting high reflectance for the unwanted portions and high absorbance for the resist, and extracting an image of scattered resist attached to the unwanted portions which are common as a base to both the image of the scattered resist-free unwanted portions which are obtained by illuminating said inspection region with a second wavelength light exhibiting high reflectance for the unwanted portions and high transmittance for the resist, and the image of the resist-attached portions.

9. A resist scattering inspection method comprising the steps of illuminating, with white light, a target inspection region including unwanted portions to which no scattered resist must be attached, and picking up a color image of the target inspection region to obtain image data and then detecting a region having the same hue and chroma as the resist on said image on the basis of the image data.

10. A resist scattering inspection apparatus comprising illumination means for illuminating, with illumination light, a target inspection region including unwanted portions to which no scattered resist must be attached, the illumination light containing a first wavelength light exhibiting high reflectance for the unwanted portions and high absorbance for the resist and a second wavelength light exhibiting high reflectance for the unwanted portions and high transmittance for the resist, and second wavelength color detection means for detecting an image having the color of the second wavelength light from images of the target inspection region which are obtained by illumination of the region with the illumination light.

11. An apparatus according to claim 10, further comprising display means for displaying an image of a detection result obtained by said second wavelength detection means.

12. An apparatus according to claim 10, wherein the unwanted portion is an inner lead portion extending into a device hole in tape automated bonding.

13. A resist scattering inspection method comprising the steps of illuminating, with illumination light, a target inspection region including unwanted portions to which no scattered resist must be attached, the illumination light exhibiting high reflectance for the unwanted portions and high absorbance for the resist, and detecting a resist attached to the unwanted portions in accordance with contrast of a target inspection region image obtained by the illumination light.

14. A resist scattering inspection apparatus comprising illumination means for illuminating a target inspection region including unwanted portions to which no scattered resist must be attached, respectively with a first wavelength light exhibiting high reflectance for the unwanted portions and high absorbance for the resist and a second wavelength light exhibiting high reflectance for the unwanted portions and high transmittance for the resist, and scattered resist detection means for extracting an image of resist-attached portions as those having lightness not more than a predetermined value from images of the target inspection region which are obtained by illumination with the first wavelength light, and extracting an image of scattered resist attached to the unwanted portions which are common as a base to both the image of the scattered resist-free unwanted portions which is obtained by illuminating said target inspection region with the second wavelength light, and the image of the resist attached portions.

15. An apparatus according to claim 14, further comprising display means for displaying an image extracted by said scattered resist detection means.

16. An apparatus according to claim 14, wherein said unwanted portions are inner lead portions protruding into a device hole in tape automated bonding, and the extraction of the image of the scattered resist attached to the unwanted portions is effected by extracting members which are present in the device hole and are common to both the image of the resist-free target inspection region which is obtained by illuminating said target inspection region with the second wavelength light, and the image of the resist-attached portions.

* * * * *